United States Patent
Dickens

(10) Patent No.: US 6,413,508 B1
(45) Date of Patent: Jul. 2, 2002

(54) GREEN LEAF VOLATILES AS SYNERGISTS FOR INSECT PHEROMONES

(75) Inventor: Joseph C. Dickens, Starkville, MS (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 08/015,260

(22) Filed: Feb. 8, 1993

Related U.S. Application Data

(63) Continuation of application No. 07/359,174, filed on May 31, 1989, now abandoned, which is a continuation-in-part of application No. 07/215,091, filed on Jul. 5, 1988, now abandoned.

(51) Int. Cl.$^7$ ............................................. A01N 25/00
(52) U.S. Cl. ........................................................ 424/84
(58) Field of Search .......................................... 424/84

(56) References Cited

U.S. PATENT DOCUMENTS 3,895,078 A * 7/1975 Gueldner et al. ........... 260/617

OTHER PUBLICATIONS

Hedin et al, J Chem Ecol, 5: 617–27, 1979.*
Visser Ann. Rev Entomology, 31, 121–44, 1986.*
Handee et al, J Economic Entomology vol. 64(6) pp. 1454–1456, 1971.*
McKibben et al, J Economic Entomology vol 64(6) pp. 1494–1495, 1971.*
Hedin et al Phytochemistry vol. 14 pp. 2088–2090, 1975.*
Pearce et al., J. Chem. Ecol. 1(1): 115–124 (1975).
McKibben et al., J. Econ. Entomol. 64(6): 1493–1495 (1971).
Light, Douglas M., et al., "Electroantennogram Responses of the Mediterranean Fruit Fly, *Ceratitis capitata*, to a Spectrum of Plant Volatiles", *Journal of Chemical Ecology*, vol. 14, No. 1, Jan. 1988, pp. 159–180.
Visser, J. H., "Host Odor Perception in Phytophagous Insects", *Ann. Rev. Entomol.*, 1986, 31, pp. 121–144.
Dickens, J. D., et al., "Green Leaf Volatiles Interrupt Aggregation Pheromone Response in Bark Beetles Infesting Southern Pines", Experientia 48 (1992), Birkhauser Verlag, CH–4010 Basel/Switzerland, pp. 523–524.
Hamilton, J. G. C., et al., "Multichemical Defense of Plant Bug *Hotea gambiae* (Westwood) (Heteroptera: scutelleridae): (E)–2–Hexenol from Abdominal Gland in Adults", *Journal of Chemical Ecology*, vol. 11, No. 10, 1985, pp. 1399–1409.
Guerin, P. M., et al., "Identification of Host Plant Attractants for the Carrot Fly, *Psila rosea*", *Journal of Chemical Ecology*, vol. 9, No. 7, 1983, pp. 843–861.
Chemical Abstracts, vol. 113, No. 208509g, 1990, p. 430, Mohri, Satoshi, et al., "Physiological Effects of Soybean Seed Lipoxygenases on Insects".
12–Nonmammalian Biochem., vol. 82, No. 152443c, 1975, p. 301, Tschinkel, Walter R., Unusual Occurrence of Aldehydes and Ketones in the Defensive Secretion of the Tenebrionid Beetle, *Eleodes beameri* .
5–Agrochemicals, vol. 101, No. 85643p, 1984, p. 213, Katsoyannos, Bryon I., et al., "Hexanol: A Potent Attractant for the Black Fig Fly, *Silba adipata*".
J.H. Borden, "Semichemical–Mediated Aggregation and Dispersion in the Coleoptera," In Insect Communication, ed. T. Lewis, pp. 123–149 (1984).
E. B. Mitchell, "Manipulation and Reduction of Boll Weevil Field Populations with Plant and Sex Attractants," Ph.D. Diss, Mississippi State University, Cover, p. 60 (1971).
D. D. Hardee et al., "Factors Affecting Activity of Grandlure, the Pheromone of the Boll Weevil, in Laboratory Bioassays," J. Econ. Entomol. 64(6): 1454–1456 (1971).
D. D. Hardee et al., "A Laboratory Technique for Bioassay of Plant Attractants for the Boll Weevil," J. Econ. Entomol. 59(1): 240–241 (1966).
J. H. Visser et al., "Isolation and Identification of Volatiles in the Foliage of Potato, *Solanum tuberosum*, A Host Plant of the Colorado Beetle, *Leptinotarsa decemlineata*," J. Chem. Ecol. 5(1): 13–25 (1979).
J. C. Dickens, "Olfaction in the Boll Weevil, *Anthonomus grandis* BOH. (Coleoptera: Curculionidea): Electroantennogram Studies," J. Chem. Ecol. 10(12): 1759–1785 (1984).
J. N. C. Van Der Pers and C. Lofstedt, "Signal–Response Relationship in Sex Pheromone Communication," In Mechanisms in Insect Olfaction, eds. T. L. Payne, M. C. Birch, and C. E. J. Kennedy, pp. 235–241 (1986).
T. L. Payne, "Bark Beetle Olfaction. III. Antennal Olfactory Responsiveness of *Dendroctonus frontalis* Zimmerman and *D. brevicomis* Le Conte (Coleoptera: Scolytidae) to Aggregation Pheromones and Host Tree Terpene Hydrocarbons," J. Chem. Ecol. 1(2): 233–242 (1973).
W. L. Roelofs, "The Scope and Limitations of the Electroantennogram Technique in Identifying Pheromone Components," In Crop Protection Agents—Their Biological Evaluation, ed. N. R. McFarlane, pp. 147–165 (1977).
P. A. Hedin et al., "Cotton Plant and Insect Constituents That Control Boll Weevil Behavior and Development," Ann. Rev. Phytochem. 10: 271–350 (1976).
K.–E. Kaissling, "Insect Olfaction," In Handbook of Sensory Physiology, vol. IV, Olfaction, ed. L. M. Biedler, pp. 351–423 (1971).
T. L. Payne, "Pheromone Perception," In Pheromones, ed. M. C. Birch, pp. 35–61 (1974).
M.M. Blight et al., Naturwissenschaften, vol. 71, (1984), p. 480.

* cited by examiner

*Primary Examiner*—Russell Travers
(74) *Attorney, Agent, or Firm*—M. Howard Silverstein; Randall E. Deck; John D Fado

(57) ABSTRACT

Green leaf volatiles were found to synergize the attractant effect of insect pheromones on boll weevils, European elm bark beetles, and Mediterranean fruit flies. Trans-2-hexen-1-ol, hexanal, trans-2-hexenal, cis-3-hexen-1-ol, and 1-hexanol were most effective. These sounds will be useful in control of insect populations.

18 Claims, No Drawings

GREEN LEAF VOLATILES AS SYNERGISTS FOR INSECT PHEROMONES

CROSS-REFERENCE TO RELATED APPLICATION

This application is a continuation, of application Ser. No. 07/359,174, filed May 31, 1989 now abandoned which is a continuation-in-part application of P.C. 6980MB, Ser. No. 07/215,091, filed Jul. 5, 1988 now abandoned.

BACKGROUND OF THE INVENTION

1. Field of the Invention

This invention relates to compounds which synergize the behavioral responses of insects induced by their attractant pheromones. These compounds may be used in combination with pheromones and insect control measures such as toxicants or traps. The compounds also extend the life of pheromone-baited traps and decrease the amount of pheromone needed.

2. Description of the Prior Art

Insect-produced volatiles, e.g., pheromones, and host plant odors, e.g., kairomones, may facilitate location of conspecifics for mating and orientation to acceptable host plants for feeding and oviposition. It is known in several insect species, especially bark beetles, that pheromones and plant odors, such as monoterpenes, may act in synergy, each enhancing the attraction of the other [Borden, in *Insect Communication*, ed. T. Lewis, Academic Press, NY, page 123 (1984)]. For example, response of *Dendroctonus brevicomis* Lec. to its aggregation pheromone is enhanced by the host monoterpene, myrcene [Bedard et al., Science 164: 1284–1285 (1969)]. Response of the boll weevil to its pheromone is enhanced by a mixture of five monoterpenes [Chang et al., Southwest. Entomol. 11: 233–241 (1986)]. The tripartite blend of a host monoterpene and two component aggregation pheromone used in chemoorientation by *D. brevicomis* was thought to increase specificity of the pheromone respone [Birch, in *Chemical Ecology of Insects*, eds. W. J. Bell and R. T. Carde, Chapman and Hall Ltd., London, pages 331–353, (1984)].

Green leaf volatiles, six-carbon alcohols and aldehydes (e.g., 1-hexanol, trans-2-hexen-1-ol, cis-3-hexen-1-ol and their corresponding aldehydes, hexanal, trans-2-hexenal, and cis-3-hexenal) are known to occur in green plants as a product of oxidative degradation of plant lipids [Visser et al., J. Chem. Ecol. 5: 13 (1979)]. Previous studies have shown these compounds to be active as host plant attractants [Visser et al., Entomol. Exp. Appl. 24: 538–549 (1978); Katsoyannos et al., Entomol. Exp. Appl. 35: 71–74 (1984)], enhancers of other host plant odors [Guerin et al., J. Chem. Ecol. 9: 843–861 (1988), indicators of fruit is ripeness [Engel et al., J. Agric. Food Chem. 36: 1003–1006 (1988); Light et al., Proc. XVIII Internat. Congr. Entomol. Abstr., 213 (1988)] or defensive secretions [Hamilton et al., J. Chem. Ecol. 11: 1399–1409 (1985)].

The attractant pheromone of the boll weevil was previously identified and shown to consist of four oxygenated monoterpenoid components [Tumlinson et al., Science 166: 1010–1012 (1969)]. The detection of green leaf volatiles by insects [Visser, Annu. Rev. Entomol. 31: 121 (1986)], including the boll weevil, has been previously shown [Dickens, J. Chem. Ecol. 10: 1759 (1984)].

The smaller European elm bark beetle, *Scolytus multistriatus* (Marsham), is a vector of Dutch elm disease which threatens elm tree populations where it occurs. Multilure (the aggregation pheromone mixture of α-multistriatin, methyl heptanol, and cubebene) [Pearce et al., J. Chem. Ecol. 1: 115–124 (1975)] trapping is used primarily as a means of removing portions of resident *S. multistriatus* populations from a given area.

The cotton plant itself and an aqueous extract of cotton leaves have been shown to increase responses of boll weevils in laboratory bioassays to grandlure, the pheromone of the boll weevil [Hardee et al., J. Eco. Ent. 64(6): 1454 (1971)]; however, among the more than 250 volatile components of cotton [Hedin et al., Annu. Rev. Phytochem. 10: 271 (1976)], the specific compounds responsible for the increased effect were not isolated or identified.

SUMMARY OF THE INVENTION

I have now discovered that members of the green leaf volatile complex, especially trans-2-hexen-1-ol, cis-3-hexen-1-ol, 1-hexanol, hexenal, and trans-2-hexanal are effective synergists for insect pheromones.

In accordance with this discovery, it is an object of the invention to provide new positions for attracting insects as an aid to insect control measures.

A further object of the invention is to provide new means to synergize the effect of insect pheromones.

A further object of the invention is to provide a means for increasing the effectiveness of insect traps for monitoring or suppressing insect populations.

Other objects and advantages of this invention will become obvious from the ensuing description.

DETAILED DESCRIPTION OF THE INVENTION

I have found that green leaf volatiles enhance the attractant pheromone response of the boll weevil, *Anthonomus grandis* Boh., the smaller European elm bark beetle, *Scolytus multistriatus* (Marsham), and the Mediterranean fruit fly, *Ceratitis capitata* Weid.

The importance of olfaction in the beavior of insects is well known. Insect-produced volatiles, e.g., pheromones, and host plant odors may facilitate location of conspecifics for mating and orientation to acceptable host plants for feeding and oviposition. Pheromones, which may be attractive alone, may be enhanced or synergized by host plant odors which show little attraction when presented alone.

A synergist is herein defined as a material that enhances the activity of other materials, so that the overall activity of the mixture is greater than the sum of the individual components.

An effective amount of a synergist is herein defined as an amount of synergist which in combination with the appropriate insect pheromone will attract a statistically greater number of insects than the sum of the pheromone and the synergist alone.

An effective synergist for an attractant pheromone is useful in several ways:

1. A synergist improves population monitoring with the pheromone not only by increasing the attractiveness of the pheromone but also by modifying the sex ratio of the insects attracted.
2. A synergist improves attractiveness of the pheromone, thus facilitating trap-out strategies.
3. An inexpensive synergist reduces the cost of insect control, since its addition to the pheromone in traps decreases the quantity of costly pheromone needed and extends the longevity of the attractive bait.

4. Pheromone traps for the boll weevil, which currently must be placed in the cotton field, will be more cost effective if a synergist makes them attractive when placed outside the cotton field.

Boll Weevils

The boll weevil is a serious pest of cotton throughout the southeastern United States, Arizona, and Central and South America. It was introduced from Mexico in the late 1800's and spread northward and eastward to areas where cotton was grown. Economic losses caused by this insect devastated cotton production in this region and required the use of large quantities of insecticides. The cost of insecticides for the control of insects on cotton and corn exceeds that for any other crops. Although the use of insecticides in the control of cotton insects is widespread, the use of currently available chemicals poses a threat both to man and his environment. Furthermore, insects have developed resistance to certain insecticides.

With the identification of the boll weevil pheromone in 1969, a tool was available to monitor boll weevil populations for directing insecticide applications and evaluating control measures. The pheromone could also potentially be used in trap-out strategies. However, the pheromone is composed of four oxygenated monoterpenes that are expensive and subject to oxidation, and no practical synergist is currently available for the pheromone.

The boll weevil is narrowly oligophagous, feeding primarily on cotton, Gossypium hirsutum L., and closely related Malvaceae. Once male boll weevils locate their host plant, feeding ensues, and they release an attractant pheromone in their frass. This pheromone is used in the Boll Weevil Eradication Program for both census and evaluation of control and/or eradication efforts. I have discovered a potent class of chemicals that, when released with the boll weevil pheromone, enhances its attraction, increases the longevity of pheromone-baited traps, and decreases the amount of pheromone needed.

This class of compounds, known as green leaf volatiles, includes six-carbon alcohols and aldehydes which are products of oxidation of plant lipids. The six-carbon chains may be saturated or unsaturated.

Specifically, trans-2-hexen-1-ol, cis-3-hexen-1-ol, and 1-hexanol, when added to traps in the field, both enhance attraction of the pheromone and prolong the attractiveness of pheromone-baited traps. Green leaf volatiles occur in all green plants and will serve to synergize or enhance behavioral responses of other insects to their attractant pheromones.

Study of individual olfactory cells from males and females by electrophysiology revealed that specific cells were responsive to stimulation with grandlure, whereas other cells were activated by volatiles emanating from a crushed cotton square. No cell responded to both stimuli. Many cells activated by volatiles emanating from the crushed cotton square could also be activated by green leaf volatiles, especially trans-2-hexen-1-ol (Tale I). Not only were these cells unresponsive to the attractant pheromone but they also did not respond to monoterpenes or sesquiterpenes found in the cotton plant.

Results of competitive experiments with a triangular array of traps showed that addition of trans-2-hexen-1-ol to grandlure significantly increased its attraction relative to grandlure alone (Table II). Trans-2-hexen-1-ol, 1-hexanol, and cis-3-hexen-1-ol alone were relatively inactive when presented in competition with the other treatments.

Results of tests with a four trap array showed that trans-2-hexen-1-ol at a dosage as low as 0.1 mg in combination with grandlure (0.8 mg) increased trap capture when in competition with grandlure (0.8 mg) alone ($P<0.10$; paired t-test) (Table III). When trans-2-hexen-1-ol was increased to 1.0 mg, enhancement of grandlure (0.8 mg) was even more apparent ($P<0.01$; paired t-test). Similarly, both 1-hexanol (1 mg) and cis-3-hexen-1-ol (1 mg) were effective synergists for grandlure (0.8 mg) when in competition with grandlure (0.8 mg) alone ($P<0.05$; paired t-test). However, when 1-hexanol and trans-2-hexen-1-ol were each presented in combination with grandlure (0.8 mg) in a competitive experiment, trans-2-hexen-1-ol in combination with grandlure (0.8 mg) was more effective than the combination with 1-hexanol. When the aldehyde, trans-2-hexenal, was released with grandlure vs grandlure alone, no significant difference was noted in trap captures. However, this was the only dosage of this compound tested, and subsequent gas chromatographic analyses showed that the aldehyde

TABLE I

Action Potentials Elicited from Single Olfactory Cells Responsive to Volatiles Emanating from a Crushed Cotton Square by Volatiles Emanating from 1 $\mu$g of Various Odorants Found in the Cotton Plant

| | Response in impulses/initial 500 msec | | | |
|---|---|---|---|---|
| Odorant | Cell #1 | Cell #2 | Cell #3 | Cell #4 |
| grandlure | 2 | 7 | 5 | 1 |
| cotton square | 68 | 7 | 18 | 15 |
| *1-hexanol | 11 | 30 | 42 | — |
| *trans-2-hexen-1-ol | 83 | 67 | 50 | 33 |
| *hexanal | 16 | 13 | — | 27 |
| *trans-2-hexenal | 27 | 24 | 1 | 38 |
| heptanal | 1 | 0 | 0 | 16 |
| nonanal | 2 | 0 | 0 | 4 |
| (-)-α-pinene | 4 | 0 | 1 | 7 |
| (-)-limonene | 0 | 0 | 2 | 1 |
| myrcene | 2 | 1 | 1 | 3 |
| nerol | 3 | 4 | 8 | 11 |
| geraniol | 1 | 3 | 5 | 0 |
| linalool | 3 | 2 | 1 | 11 |
| α-bisabolol | 3 | 12 | 3 | 2 |
| β-bisabolol | 3 | 3 | 5 | 2 |
| β-caryophyllene | 2 | 2 | 0 | 1 |
| gossonerol | 3 | — | — | 12 |
| benzaldehyde | 3 | 0 | 1 | 0 |

*Denotes green leaf volatile.

TABLE II

Mean Number of Boll Weevils Captured in Three Replicates of Competitive Field Tests in Mississippi of Three Simultaneous Treatments in Triangular Trap Array

| Treatment | Mean Trap Capture* | % Total | Sex Ratio (M:F) |
|---|---|---|---|
| grandlure (3 mg) | 6.3 A | 28.8 | 2.8:1 |
| trans-2-hexen-1-ol (100 mg) | 1.3 A | 5.9 | 0.3:1 |
| grandlure (3 mg) + trans-2-hexen-1-ol (100 mg) | 14.3 B | 65.3 | 1.3:1 |
| grandlure (3 mg) | 4.7 A | 29.8 | 1.8:1 |
| 1-hexanol (100 mg) | 0 A | 0 | 0:0 |
| grandlure (3 mg) + 1-hexanol (100 mg) | 11.0 B | 70.2 | 0.9:1 |
| grandlure (3 mg) | 5.3 A | 36.4 | 0.6:1 |

TABLE II-continued

Mean Number of Boll Weevils Captured in Three
Replicates of Competitive Field Tests in Mississippi of
Three Simultaneous Treatments in Triangular Trap Array

| Treatment | Mean Trap Capture* | % Total | Sex Ratio (M:F) |
|---|---|---|---|
| cis-3-hexen-1-ol (100 mg) | 0 B | 0 | 0:0 |
| grandlure (3 mg) + cis-3-hexen-1-ol (100 mg) | 9.3 A | 63.6 | 1.8:1 |

*Means followed by different letters are significantly different (Duncan's Multiple Range Test; $P < 0.05$).

TABLE III

Mean Number of Boll Weevils Captured in Five
Replicates of Competitive Field Tests in Mississippi
of Two Simultaneous Treatments in Four Trap Array

| Treatment Pair | Mean Trap Capture | % Total | Sex Ratio (M:F) |
|---|---|---|---|
| grandlure (0.8 mg) vs | 35.0 | 44.1 | 0.9:1 |
| grandlure (0.8 mg) + trans-2-hexen-1-ol (0.1 mg) | 44.4* | 55.9 | 0.8:1 |
| grandlure (0.8 mg) vs | 20.8 | 38.7 | 1.0:1 |
| grandlure (0.8 mg) + trans-2-hexen-1-ol (1.0 mg) | 33.0*** | 61.3 | 0.6:1 |
| grandlure (0.8 mg) vs | 13.0[1] | 37.9 | 1.0:1 |
| grandlure (0.8 mg) + 1-hexanol (1.0 mg) | 21.3** | 62.1 | 1.3:1 |
| grandlure (0.8 mg) + 1-hexanol (1.0 mg) vs | 17.7[1] | 40.5 | 0.7:1 |
| grandlure (0.8 mg) + trans-2-hexen-1-ol (1.0 mg) | 26.0* | 59.5 | 1.0:1 |
| grandlure (0.8 mg) vs | 17.2 | 41.3 | 1.8:1 |
| grandlure (0.8 mg) + cis-3-hexen-1-ol (1.0 mg) | 24.4** | 58.7 | 1.2:1 |
| grandlure (0.8 mg) vs | 23.0 | 54.8 | 1.6:1 |
| grandlure (0.8 mg) + trans-2-hexenal (1.0 mg) | 19.0 | 45.2 | 1.8:1 |
| grandlure (0.8 mg) vs | 31.4 | 52.0 | 1.0:1 |
| grandlure (0.8 mg) + cis-2-hexen-1-ol (1.0 mg) | 29.0 | 48.0 | 1.3:1 |

[1]Mean of three replicates.
*$P < 0.10$.
**$P < 0.05$.
***$P < 0.01$ (paired t-test).

had in part been degraded by the field conditions in which it was released. Cis-2-hexen-1-ol, a questionable member of the general green leaf volatile complex, also showed no synergism. In these competitive experiments, comparisons between numbers of weevils captured are appropriate only between treatments tested simultaneously.

In competitive field tests in cotton fields, our results showed that the synergist, trans-2-hexen-1-ol, at 1 mg, 10 mg, and 100 mg in combination with grandlure at 1 mg captured more weevils of both sexes than grandlure alone at 1 mg ($P<0.01$; paired t-test) (Tale IV). It seed that the synergist was especially effective with lower populations, such as occurred in fields containing trans-2-hexen-1-ol at 1 mg and 100 mg.

An experiment to determine the longevity of attractiveness of traps baited with grandlure (1 mg) and grandlure (1 mg)+trans-2-hexen-1-ol revealed that the number of boll weevils captured in each field with grandlure alone decreased from the first to the second wk (Table V). Similarly, the total number of weevils captured by grandlure+trans-2-hexen-1-ol at the lowest dosage tested (1 mg) also decreased during this period. However, when grandlure was combined with trans-2-hexen-1-ol at 10 mg and 100 mg, trap capture actually increased with increasing dosages of the synergist from wk #1 to wk #2. It should also be noted that in each case the percent of weevils captured by grandlure+trans-2-hexen-1-ol vs grandlure creased from wk #1 to wk #2, and more weevils were captured with grandlure+trans-2-hexen-1-ol than with grandlure alone over the duration of the test.

The results of my experiments in the cotton field were surprising and indicate that trans-2-hexen-1-ol not only enhances trap capture when presented with grandlure but also extends the life of grandlure-baited traps and decreases the amount of grandlure needed.

TABLE IV

Total Number and Sex Ratio of Boll Weevils Captured
in Competitive Field Tests During 4-Week Test Period in Three
Cotton Fields in Mississippi with Traps Baited with Grandlure
vs Grandlure + trans-2-hexen-1-ol
at Three Different Dosages

| Treatment | Total Trap Capture | % Total | Sex Ratio (M:F) |
|---|---|---|---|
| grandlure (1 mg) vs | 269 | 42.4 | 1.1:1 |
| grandlure (1 mg) + trans-2-hexen-1-ol (1 mg) | 369 | 57.6 | 1.6:1 |
| grandlure (1 mg) vs | 864 | 46.5 | 1.5:1 |
| grandlure (1 mg) + trans-2-hexen-1-ol (10 mg) | 993 | 53.5 | 1.6:1 |
| grandlure (1 mg) vs | 247 | 41.7 | 1.2:1 |
| grandlure (1 mg) + trans-2-hexen-1-ol (100 mg) | 346 | 58.3 | 1.1:1 |

TABLE V

Total Number of Boll Weevils Captured in
Competitive Field Tests Over 2 Weeks in Three
Cotton Fields in Mississippi to Determine the
Longevity of Attractiveness of Traps Baited with
Grandlure vs Grandlure + trans-2-hexen-1-ol
at Three Different Dosages

| | Trap Capture (%) | | |
|---|---|---|---|
| Treatment | First Week | Second Week | Total |
| grandlure (1 mg) vs | 184 (43.8) | 110 (39.1) | 294 (41.9) |
| grandlure (1 mg) + trans-2-hexen-1-ol (1 mg) | 236 (56.2) | 171 (60.9) | 407 (58.1) |
| grandlure (1 mg) vs | 361 (48.8) | 235 (34.1) | 596 (41.7) |

TABLE V-continued

Total Number of Boll Weevils Captured in Competitive Field Tests Over 2 Weeks in Three Cotton Fields in Mississippi to Determine the Longevity of Attractiveness of Traps Baited with Grandlure vs Grandlure + trans-2-hexen-1-ol at Three Different Dosages

| Treatment | Trap Capture (%) | | |
|---|---|---|---|
| | First Week | Second Week | Total |
| grandlure (1 mg) + trans-2-hexen-1-ol (10 mg) | 379 (51.2) | 454 (65.9) | 833 (58.3) |
| grandlure (1 mg) vs | 174 (44.4) | 70 (18.5) | 244 (31.7) |
| grandlure (1 mg) + trans-2-hexen-1-ol (100 mg) | 218 (55.6) | 308 (81.5) | 526 (68.3) |

Mediterranean Fruit Flies

Although numerous components of the attractant produced by Mediterranean fruit fly males have been chemically identified [Baker et al., J. Chem. Soc. Chem. Comm., 824–825 (1985); Jang et al., Entomol. Exp. Appl. (in press)], the active constituents have not been fully resolved. Therefore, the pheromonal odor of calling males was tested in competition with male odor plus a combination of green leaf volatiles in a laboratory flight tunnel. Green leaf volatiles increased the number of landings made by female flies on the odor source relative to male odor alone, as well as increasing the mean maximum number of flies on the spheres [Table VI(c)]. In fact, the major green leaf volatile of the blend, trans-2-hexenal, alone enhanced response of female medflies to male odor. Similar to the boll weevil and smaller elm bark beetle, little or no response was elicited by the green leaf volatiles alone.

Bark Beetles

When 1-hexanol or hexanal or a mixture of 1-hexanol and hexanal were released with multilure, the multicomponent aggregation pheromone of *S. multistriatus* [Pearce, supra], captures of bark beetles in traps were increased relative to the pheromone alone [Table VI(b)]. Neither the boll weevil nor the smaller elm bark beetle were attracted to traps baited with the green leaf volatiles alone (Tables II and VI).

The potency of these synergized pheromone compositions dictates that they be applied in conjunction with a suitable inert carrier or vehicle as known in the art. Of particular interest are those which are agronomically acceptable. Alcohols, glycols, ketones, esers, aqueous mixtures, and solid carriers such as clays or cellulose are illustrative of suitable carriers. The synergized pheromone compositions may be used in a number of ways; for example, in combination with pesticides to kill the insects or in traps to monitor population changes. Other formulations and methods of use will be obvious to skilled artisans.

TABLE VI

Attraction of the *Anthonomus grandis*, *Scolytus multistriatus*, and *Ceratitis capitata* to Their Pheromone Alone, and Combination of Pheromone and Green Leaf Volatiles in Competitive Behavioral Tests

| Competitive Treatments | Mean % Trap Capture |
|---|---|
| a. *Anthonomus grandis* | |
| grandlure (2.5 mg) | 39.7 |
| vs | |
| grandlure (2.5 mg) + trans-2-hexen-1-ol (10 mg) | 60.3* |

| Competitive Treatments | Mean % Trap Capture[1] |
|---|---|
| b. *Scolytus multistriatus* | |
| unbaited trap | 0.3a |
| vs | |
| hexanal (10 mg) | 0.3a |
| vs | |
| 1-hexanol (10 mg) | 0a |
| vs | |
| hexanal (10 mg) + 1-hexanol (10 mg) | 1.3a |
| vs | |
| multilure | 14.9b |
| vs | |
| multilure + hexanal (10 mg) | 22.0bc |
| vs | |
| multilure + 1-hexanol (10 mg) | 25.0bc |
| vs | |
| multilure + hexanal (10 mg) + 1-hexanol (10 mg) | 40.8c |

| Competitive Treatments | Mean # landings | Mean maximum # of flies on sphere |
|---|---|---|
| c. *Ceratitis capitata* | | |
| male odor | 7.60 | 4.40 |
| vs | | |
| male odor + glv | 19.80** | 8.20* |
| male odor | 16.50 | 6.00 |
| vs | | |
| male odor + trans-2-hexenal | 28.70* | 9.50** |

*$P < 0.05$
**$P < 0.01$
[1]Means followed by different letters are significantly different (Duncan's Multiple Range Test; $P < 0.05$)

The synergized pheromone compositions encompassed herein are effective in attracting a variety of organisms. Without desiring to be limited thereto, pests of particular interest known to be susceptible to treatment are agronomically important insects, especially the boll weevil, *Anthonomus grandis* BOH; the European elm bark beetle, *Scolytus multistriatus*; and the Mediterranean fruit fly, *Ceratitis capitata*.

A typical synergized pheromone opposition contemplated by this invention for use in an inert trap comprises trans-2-hexen-1-ol 0.1 mg to 100 mg, preferably 1.0 mg; grandlure 0.1 mg to 10 mg, preferably 0.8 mg, combined with a suitable amount of an inert carrier.

Without desiring to be bound by any particular theory of operation, it is believed that the green leaf volatiles act by stimulating certain specific olfactory cells in the insect antenna.

The following examples are intended only to further illustrate the invention and are not intended to limit the scope of the invention, which is defined by the claims.

EXAMPLE 1

Materials and Methods

Insects.

Adult *A. grandis* used in field releases and electrohysiological experiments were obtained from a small laboratory colony annually infused with feral insects maintained at the USDA-ARS Boll Weevil Research Unit. Upon emrgence, insects were sexed and fed cotton squares. For electrophysiological studies, groups of five insects of the same sex were maintained on moist filter paper in petri dishes until use. For field experiments, groups of 50 insects of the same sex were held in paper cartons (ca. 0.5 L) with screen tops. Insects used in field releases were 6- to 13-days postemergence. All insets were held in incubators at 26° C. under a photoregime of 16 hrs of light (ca. 700 lux) and 8 hrs of darkness.

Chemicals.

Grandlure is composed of four compounds. Compound I is (+)-cis-2-isopropenyl-1-methylcyclobutaneethanol; II, cis-3,3-$\Delta^{1,\beta}$cyclohexaneethanol; III, cis-3,3-dimethyl-$\Delta^{1,\alpha}$-cyclohexaneacetaldehyde; and IV, trans-3,3-dimethyl-$\Delta^{1,\alpha}$-cyclohexaneacetaldehyde. These were obtained in >95% purity from Albany International, Controlled Release Division, Buckeye, Ariz. For certain field tests with released weevils, compounds were prepared as 10 $\mu g/\mu L$ dilutions in hexane. The ratio of the pheromone components used in these studies [I(4):II(3):III+IV(1)] approximated that of the natural pheromone as identified from the frass produced by male boll weevils [Tumlinson et al., supra]. For other field tests in which cigarette filters were used as release devices, the odorants were diluted in the following mixture: polyethylene glycol 1,000, 20%; methanol, 42.5%; glycerol, 25%; and distilled water, 12.5% [McKibben et al., J. Econ. Entomol. 73: 250–251 (1980)]. The ratio of pheromone used in the cigarette filters was [I(3):II(4):III+IV(3)] that currently used in the Boll Weevil Eradication Program. This ratio was chosen for use in the Boll Weevil Pogrom based on economic considerations, even though the ratio of components in the natural attractant is more attractive in competitive tests [Hardee et al., Environ. Entomol. 3: 135 (1974)].

trans-2-Hexen-1-ol and 1-hexanol as obtained from Aldrich Chemical Co., Milwaukee, Wis., were 97% and 98% chemical purity, respectively. Other cotton volatiles [Hedin et al., Toxicol. Environ. Chem. Rev. 1: 291 (1973)] used in single-cell studies (purity given in parenthesis) and sources were as follows: hexanal (99%), heptanal (95%), nonanal (98%), (−)-$\alpha$-pinene (98%), (−)-limonene (97%), myrcene (85%), linalool (99%), benzaldehyde (>98%), all obtained from Aldrich Chemical Co., Milwaukee, Wis.; nerol (>65%) and geraniol (>90%), both obtained from Pfaltz & Bauer, Inc., Stamford, Conn. $\alpha$-bisabolol (92%) and $\beta$-bisabolol (83%), both obtained from P. A. Hedin, USDA-ARS, Crop Science Research Laboratory, Mississippi State, Miss.; gossonerol (>98%), obtained from H. J. Williams, Department of Entomology, Texas A&M University; $\beta$-caryophyllene (90.2%) obtained from ICN-K&K Laboratories, Plainview, N.Y. Multilure was obtained from DeWill Corp., Elmhurst, Ill.

EXAMPLE 2

Electrophysiology

Single-cell recording techniques are described in detail elswhere [Dickens, Mitt. Schweiz. Entomol. Ges. 52: 203 (1979); Dickens et al., J. Chem. Ecol. 10: 583 (1984)]. In brief, microelectrodes used for recordings were constructed from 50.8 $\mu m$ diameter tungsten wire electrolytically sharpened to a tip of 1–2 $\mu m$. The recording electrode was positioned under optical control (150–200 X) with a Leitz high-power micromanipulator near either the base of one of the three sensory bands encircling the club, or the base of an individual sensillum just distal to each sensory band region. The ground electrode was inserted in either the rostrum or distal end of the scape. Action potentials were amplified and conditioned by a Grass P-15 preamplifier and Tektronix 5A22N amplifier prior to visualization on a Tektronix 5223 digitizing oscilloscope. The signal then passed through a Teac R51-D data recorder for recording on cassette tapes prior to visualization on a Tektronix 5111 analog oscilloscope. Data were photographed from the analog oscilloscope with a Tektronix C-5C oscilloscope camera. Trains of action potentials were counted visually.

Upon obtaining a single cell preparation, odorous stimuli were presented every 3 min. Single-cell activity was observed to recover to a prestimulus level after this time period. The first two stimuli tested were volatiles emanating from 1 $\mu g$ of grandlure, followed by volatiles emanating from a crushed cotton square. These two stimuli served to determine whether the cell was activated by the attractive pheromone of the boll weevil and/or volatiles emanating from its food source. Results are shown in Table I.

EXAMPLE 3

Competitive Field Tests with Released Weevils

Two series of field tests were performed involving released boll weevils, in which grandlure was placed in competition with grandlure + the synergist. In the first series of experiments, a triangular array of traps was used. One trap was placed at each corner of a 20 m equilateral triangle (total of three traps). The three treatments released in this triangular array of traps were: 1) grandlure 3 mg; 2) grandlure 3 mg+synergist 100 mg; and 3) synergist 100 mg. The three synergists tested in these experiments were: trans-2-hexen-1-ol, 1-hexanol, and cis-3-hexen-1-ol. Cigarette filters were used to release the experimental odorants. One hundred insets (50 males and 50 females) were released along a line 20 m from each side of the triangle (300 insects total) at ca. 1000 hrs prior to baiting of the traps at 1200 hrs. Traps were check and insects were removed at 1400 hrs, 1600 hrs, and 1800 hrs, the times at which the test was terminated. Results are shown in Table II.

The second series of experiments involved an array of four traps. One trap was placed at each corner (four traps total) of a 20-m square. The two treatments being tested simultaneously in this competitive arrangement were placed alternately in the traps, i.e., the two traps baited with the same treatment were located diagonally from each other. Odorants diluted in hexane were released from glass capillaries placed in small vials in a container in each trap. One hundred insects (50 males+50 females) were released along a line 20 m from each side of the square (400 insects total) at 1400 hrs. Traps were then immediately baited. In each test, traps were checked and insects were removed at 1530 hrs and 1700 hrs on the day of release, and before 0900 hrs the next day (the time at which the test was terminated) in order to remove those insects which might have responded prior to darkness on the day of release. Treatments tested in this competitive arrangement were: a) grandlure 0.8 mg vs grandlure 0.8 mg+trans-2-hexen-1-ol 0.1 mg; b) grandlure 0.8 mg vs grandlure 0.8 mg+trans-2-hexen-1-ol 1.0 mg; c) grandlure 0.8 mg vs grandlure 0.8 mg+1-hexanol 1.0 mg; d) grandlure 0.8 mg vs grandlure 0.8 mg+cis-3-hexen-1-ol 1.0 mg; e) grandlure 0.8 mg+trans-2-hexen-1-ol 1.0 mg vs grandlure 0.8 mg+1-hexanol 1.0 mg; f) grandlure 0.8 mg vs grandlure 0.8 mg+trans-2-hexenal 2.0 mg; and g) grandlure 0.8 mg vs grandlure 0.8 mg+cis-hexen-1-ol 1.0 mg. Results are shown in Table III.

EXAMPLE 4

Competitive Field Tests in Mississippi cotton Fields

Three cotton fields were used in this study to determine the effectiveness of trans-2-hexen-1-ol in synergizing grandlure in a practical situation. The experimental design consisted of placing four traps at the corners of a 20-m square within a cotton field of ca. 1 acre. Four additional traps were placed a few meters outside the cotton field, located near imaginary diagonal lines extending through the corners of the square within the field. Each trap contained a cigarette filter with 1 mg of grandlure. Cigarette filters containing trans-2-hexen-1-ol were placed alternately in the traps. The result resembled an "X" array of traps placed across each field with each arm of the "X" consisting of four traps, two within and two outside of the field. Traps within one arm contained grandlure 1 mg alone; those within the other arm were baited with grandlure 1 mg+trans-2-hexen-1-ol at a particular dosage. Only one dosage of the synergist occurred in each field. Dosages of trans-2-hexen-1-ol tested were: 1 mg, 10 mg, and 100 mg. Traps were freshly baited each week and checked daily at 1500 hrs for 3 days and at the end of the week.

An additional experiment using the same experimental trap design as above was performed to determine the longevity of attractiveness of traps baited with grandlure 1.0 mg alone and with grandlure 1 mg+trans-2-hexen-1-ol at 1 mg, 10 mg, and 100 mg. In this experiment, baits remained in the traps for 2 wks, and weevils were collected daily at 1500 hrs for the first 3 days of each week and at the end of each week. Results are shown in Tables IV and V.

The efficacy of the synergist in enhancing response of over-wintered boll weevils to grandlure was evaluated during the first 3 wks of May 1988, prior to the planting of cotton. In this experiment, the synergist trans-2-hexen-1-ol at 10 mg was released from a cigarette filter, in combination with a Hercon wafer formulation of grandlure at 2.5 mg. The grandlure formulation remained in the trap for the entire 3-wk period, while the cigarette filter containing the synergist was changed each week. During both the first and second weeks, trap captures increased for both the pheromone alone and for the pheromone+the synergist, presumably reflecting increasing numbers of boll weevils emerging from over-wintering sites (Table VII). However, while trap captures continued to increase for the pheromone+synergist during the third week, the number of boll weevils captured by the pheromone alone declined. Thus, not only did the synergist extend the effectiveness of the pheromone over a 3-wk period but the combination also captured an increasing number of boll weevils, thus effectively monitoring spring emergence.

EXAMPLE 5

Field Tests with Boll Weevils in Arizona

Since boll weevils in this region differ genetically from those in the southeastern United States [Burke, Texas Agric. Exp. Sta. Tech. Rep., 152 pp. (1968)], these tests were performed to determine if green leaf volatiles would also enhance capture of Arizona boll weevils in traps baited with the aggregation pheromone.

TABLE VII

Total Number of Over-Wintered Boll Weevils Captured in Competitive Field Tests Over 3 Weeks in Traps Baited with Grandlure (Hercon Wafer) vs Grandlure (Hercon Wafer) + trans-2-hexen-1-ol and Placed Along the Edge of Fields Planted with Cotton During the Previous Year in Mississippi

| Treatment | First Week | Second Week | Third Week | Total |
|---|---|---|---|---|
| grandlure (2.5 mg) vs | 6 | 23 | 9 | 38 |
| grandlure (2.5 mg) + trans-2-hexen-1-ol (10 mg) | 13 | 31 | 42 | 86 |

In the initial field experiment, 24 traps were placed 30 m apart in a straight line along a road near Phoenix and were baited with four different treatments: 1) grandlure 1 mg; 2) grandlure 1 mg+trans-2-hexen-1-ol 1 mg; 3) grandlure 1 mg+trans-2-hexen-1-ol 10 mg; 4) grandlure 1 mg+trans-2-hexen-1-ol 100 mg. All compounds were released from cigarette filters after mixing in a solution to retard their rate of release, as previously described [McKibben et al., supra]. Treatments were arranged in six blocks with the four treatments randomized within each block. Traps were checked the next day. Results from this initial experiment (Table VIII) showed in each instance that addition of the green leaf volatile, trans-2-hexen-1-ol, enhanced trap capture over grandlure alone.

A second field experiment was performed, in which the 10 mg "Hercon" wafer formulation of grandlure currently used in the Boll Weevil Eradication Program was tested against 5 mg of the same formulation in combination with 10 mg of trans-2-hexen-1-ol released from a cigarette filter, as previously described. The two treatments were alternated among 24 traps placed 30 m apart in a straight line. Traps were checked and weevils were removed daily over the 2w test period. The following results were obtained, as shown in Table IX.

There was no significant difference in attractiveness between the 5-mg dose of grandlure released with 10 mg of trans-2-hexen-1-ol and the 10-mg dose of grandlure in current use in the Boll Weevil Eradication Program.

In a third field experiment, 20 cotton fields were selected. Three traps were placed at least 100 m apart along the edge of each field (60 traps total). The three traps were baited with one of the following treatments: 1) a 10-mg grandlure "Hercon" wafer; 2) 5 mg of grandlure in the same "Hercon" formulation; 3) the 5-mg grandlure

TABLE VIII

Total Number of Boll Weevils Captured in 24 Traps Placed in a Straight Line Baited with Grandlure Alone or Grandlure + trans-2-hexen-1-ol in Competitive Field Test in Arizona. Treatments were Arranged in Six Blocks with the Four Treatments Randomized within Each Block

| Treatment | Total Trap Capture |
|---|---|
| grandlure (1 mg) | 53 |
| grandlure (1 mg) + trans-2-hexen-1-ol (1 mg) | 64 |
| grandlure (1 mg) + trans-2-hexen-1-ol (10 mg) | 73 |

TABLE VIII-continued

Total Number of Boll Weevils Captured in
24 Traps Placed in a Straight Line Baited with
Grandlure Alone or Grandlure + trans-2-hexen-1-ol in
Competitive Field Test in Arizona. Treatments were
Arranged in Six Blocks with the Four Treatments
Randomized within Each Block

| Treatment | Total Trap Capture |
|---|---|
| grandlure (1 mg) + trans-2-hexen-1-ol (100 mg) | 58 |

TABLE IX

Total Number of Boll Weevils Captured in
Traps Baited with 10 mg of Grandlure vs 5 mg of
Grandlure + 10 mg of trans-2-hexen-1-ol Over
2-Week Test Period in Arizona

| Treatment | Mean Daily Trap Capture (Range) |
|---|---|
| grandlure (10 mg) | 118 (12, 346) |
| grandlure (5 mg) + trans-2-hexen-1-ol (10 mg) | 103 (20, 355) | formulation+10 mg of trans-2-hexen-1-ol. The traps were checked daily and weevils were removed for the next 2 days. The results are shown in Table X.

It is apparent that under these conditions the addition of trans-2-hexen-1-ol to grandlure enhanced its attractiveness aver the 10-mg grandlure treatment.

EXAMPLE 6

Field Test with Boll Weevils in Mississippi

Mean % trap captures were calculated from competitive field tests during a 6-wk test period in Monroe Co., Miss. Total number of *A. grandis* captured was 3095. One hundred traps were placed randomly throughout the county; one-half (50) were baited with each treatment. Grandlure consisted of compounds I:II:III+IV [Tumlinson et al., supra] in ratio 3:4:3 commercially formulated by Scentry Inc., Tucson, Ariz. trans-2-Hexen-1-ol was released from cigarette filters after dilution in 0.5 ml. of a solution to retard its release [McKibben et al., supra]. Mean % weekly trap captures were compared by a paired t-test [Ostle, *Statistics in Research*, The Iowa State University Press, Ames, Iowa (1963)]. * –P<0.05. Results are shown in Table VI(a).

EXAMPLE 7

Field Test with Bark Beetles

Mean % trap captures were calculated from competitive field tests during a 4-wk test period on campus of the University of Maine, Orono, Me. Total number of *S. multistriatus* captured was 423. Multilure consisted of α-multistriatin, methyl heptanol, and cubebene as obtained commercially from Dewill Corp., Elmhurst, Ill. Both 1-hexanol and hexanal were released from cigarette filters after dilution in the m previously described [McKibben, supra]. Mean weekly trap captures were compared by Duncan's multiple range test [Duncan, Biometrics 11: 1–42 (1955)]. Results are reported in Table VI (b).

TABLE X

Total Number of Boll Weevils Captured in Traps
Baited with Two Dosages of Grandlure and Grandlure +
trans-2-hexen-1-ol and Placed Around 20 Cotton
Fields in Arizona

| | Total Trap Capture | |
|---|---|---|
| Treatment | Day 1 | Day 2 |
| grandlure (10 mg) | 145 | 61 |
| grandlure (5 mg) | 196 | 75 |
| grandlure (5 mg) + trans-2-hexen-1-ol (10 mg) | 249 | 90 |

EXAMPLE 8

Mediterranean Fruit Flies

Flies were assayed in a rectangular glass wind tunnel (90 cm×90 cm×280 cm; flow rate=20 cm/sec) using laboratory-reared 5- to 7-day-old female *C. capitata*. The odor from 100 male *C. capitata* (30–50% calling) was obtained, and split through "Teflon" tubing to a secondary container containing the green leaf odor [either 100 μL of a 0.05% mixture in paraffin oil of trans-2-hexen-1-ol, 1-hexanol, cis-3-hexen-1-ol, trans-2-hexenal, and hexanal at a ratio of 158:100:63:24:11 (=glv, green leaf volatiles); or 100 μL of a 10% solution in silicon oil of trans-2-hexenal alone]. The odors were released into the wind tunnel via "Teflon" tubing to 7diameter yellow plastic spheres [McInnis, J. Econ. Entomol. (in press)] with multiple holes to allow odors to emanate. Fifty flies were released 200 cm downwind from the source spheres, and both the number of flies on the spheres at a given time, and total number of landings by the flies were recorded during a 30-min test period. The test with the green leaf volatile blend was replicated five times; the test with trans-2-hexenal was replicated six times. Results were compared using a paired t-test [Ostle, supra] and are shown in Table VI(c).

It is understood that the foregoing detailed description is given merely by way of illustration and that modifications and variations may be made therein without departing from the spirit and scope of the invention.

I claim:

1. A synergistic composition for attracting insects selected from the group consisting of European elm bark beetles, Mediterranean fruit flies and boll weevils comprising an insect pheromone attractant for an insect selected from the group consisting of European elm bark beetles, Mediterranean fruit flies and boll weevils, and an isolated six-carbon-containing alcohol or aldehyde plant volatile selected from the group consisting of trans-2-hexen-1-ol, 1-hexanol, hexanal, trans-2-hexenal, cis-3-hexen-1-ol, and mixtures thereof, wherein said six-carbon-containing alcohol or aldehyde plant volatile is in an amount effective to synergistically increase the attractancy of said insect pheromone to said insects.

2. A composition as described in claim 1 wherein said pheromone is a mixture consisting essentially of: (I) (+)-cis-2-isopropenyl-1-methylcyclobutaneethanol; (II) cis-3,3-dimethyl-$\Delta^{1,\beta}$-cyclohexaneethanol; (III) cis-3,3-dimethyl-$\Delta^{1,\alpha}$-cyclohexaneacetaldehyde; and (IV) trans-3,3-dimethyl-$\Delta^{1,\alpha}$-cyclohexaneacetaldehyde in the approximate ratio of I(4):II(3):III+IV(1).

3. A composition as described in claim 1 wherein said pheromone is a mixture of α-multistriatin, methyl heptanol and cubebene.

4. A composition as described in claim 1 wherein said alcohol is trans-2-hexen-1-ol.

5. A composition as described in claim 1 wherein said alcohol is 1-hexanol.

6. A position as described in claim 1 wherein said aldehyde is hexanal.

7. A composition as described in claim 1 wherein said aldehyde is trans-2-hexenal.

8. A composition as described in claim 1 wherein said alcohol is cis-3-hexen-1-ol.

9. A method for synergistically attracting insects selected from the group consisting of European elm bark beetles, Mediterranean fruit flies and boll weevils comprising exposing said insects to a bait comprising an insect pheromone attractant for an insect selected from the group consisting of European elm bark beetles, Mediterranean fruit flies and boll weevils, and an isolated six-carbon-containing alcohol or aldehyde plant volatile selected from the group consisting of trans-2-hexen-1-ol, 1-hexanol, hexanal, trans-2-hexenal, cis-3-hexen-1-ol, and mixtures thereof, wherein said six-carbon-containing alcohol or aldehyde plant volatile is in an amount effective to synergistically increase the attractancy of said insect pheromone to said insects.

10. A method as described in claim 9 wherein said pheromone is a mixture consisting essentially of: (I) (+)-cis-2-isopropenyl-1-methylcyclobutaneethanol; (II) cis-3,3-dimethyl-$\Delta^{1,\beta}$cyclohexaneethanol; (III) cis-3,3-dimethyl-$\Delta^{1,}$$_\alpha$cyclohexaneacetaldehyde; and (IV) trans-3,3-dimethyl-$\Delta^{1,}$$\alpha$-cyclohexaneacetaldehyde in the approximate ratio of I(4):II(3):III+IV(1) or I(3):II(4):III+IV(3).

11. A method as described in claim 9 wherein said pheromone is a mixture of $\alpha$-multistriatin, methyl heptanol and cubebene.

12. A method as described in claim 9 wherein said alcohol is trans-2-hexen-1-ol.

13. A method as described in claim 9 wherein said alcohol is 1-hexanol.

14. A method as described in claim 9 wherein said aldehyde is hexanal.

15. A method as described in claim 9 where in said aldehyde is trans-2-hexenal.

16. A method as described in claim 9 wherein said alcohol is cis-3-hexen-1-ol.

17. A composition as described in claim 1 wherein said pheromone is the pheromone attractant for said Mediterranean fruit flies.

18. A method as described in claim 10 wherein said pheromone is the pheromone attractant for said Mediterranean fruit flies.

* * * * *